United States Patent
Plihal et al.

(10) Patent No.: US 10,267,748 B2
(45) Date of Patent: Apr. 23, 2019

(54) OPTIMIZING TRAINING SETS USED FOR SETTING UP INSPECTION-RELATED ALGORITHMS

(71) Applicant: KLA-Tencor Corporation, Milpitas, CA (US)

(72) Inventors: Martin Plihal, Pleasanton, CA (US); Erfan Soltanmohammadi, San Jose, CA (US); Saravanan Paramasivam, Chennai (IN); Sairam Ravu, Chennai (IN); Ankit Jain, Ballston Spa, NY (US); Sarath Shekkizhar, Mountain View, CA (US); Prasanti Uppaluri, Saratoga, CA (US)

(73) Assignee: KLA-Tencor Corp., Milpitas, CA (US)

( * ) Notice: Subject to any disclaimer, the term of this patent is extended or adjusted under 35 U.S.C. 154(b) by 5 days.

(21) Appl. No.: 15/782,820

(22) Filed: Oct. 12, 2017

(65) Prior Publication Data

US 2018/0106732 A1 Apr. 19, 2018

Related U.S. Application Data

(60) Provisional application No. 62/477,248, filed on Mar. 27, 2017.

(30) Foreign Application Priority Data

Oct. 17, 2016 (IN) .............................. 2016/41035490

(51) Int. Cl.
*G06N 5/00* (2006.01)
*G01N 21/55* (2014.01)
(Continued)

(52) U.S. Cl.
CPC ......... *G01N 21/9501* (2013.01); *G01N 21/55* (2013.01); *G01N 21/8803* (2013.01);
(Continued)

(58) Field of Classification Search
CPC .. G06N 3/08; G06N 3/04; G06K 9/66; G06K 9/6267; G06T 7/0004; G01N 21/9501; G01N 21/55
(Continued)

(56) References Cited

U.S. PATENT DOCUMENTS 8,126,255 B2 2/2012 Bhaskar et al.
8,664,594 B1 4/2014 Jiang et al.
(Continued)

FOREIGN PATENT DOCUMENTS

JP 2008-082821 4/2008

OTHER PUBLICATIONS

International Search Report and Written Opinion for PCT/US2017/057029 dated Jan. 31, 2018.
(Continued)

*Primary Examiner* — David P Porta
*Assistant Examiner* — Meenakshi S Sahu
(74) *Attorney, Agent, or Firm* — Ann Marie Mewherter (57) ABSTRACT

Methods and systems for training an inspection-related algorithm are provided. One system includes one or more computer subsystems configured for performing an initial training of an inspection-related algorithm with a labeled set of defects thereby generating an initial version of the inspection-related algorithm and applying the initial version of the inspection-related algorithm to an unlabeled set of defects. The computer subsystem(s) are also configured for altering the labeled set of defects based on results of the applying. The computer subsystem(s) may then iteratively re-train the inspection-related algorithm and alter the labeled set of defects until one or more differences between results produced by a most recent version and a previous version of the algorithm meet one or more criteria. When the one or more differences meet the one or more criteria, the most recent version of the inspection-related algorithm is outputted as the trained algorithm.

20 Claims, 4 Drawing Sheets

(51) Int. Cl.
*G01N 21/88* (2006.01)
*G01N 21/95* (2006.01)
*G06N 99/00* (2010.01)
*G01N 21/956* (2006.01)

(52) U.S. Cl.
CPC ....... *G01N 21/8851* (2013.01); *G06N 99/005* (2013.01); *G01N 2021/8854* (2013.01); *G01N 2021/95676* (2013.01); *G06N 5/003* (2013.01)

(58) Field of Classification Search
USPC ............. 250/336.1; 382/149, 144, 192, 224; 702/56
See application file for complete search history.

(56) References Cited

U.S. PATENT DOCUMENTS

| | | | |
|---|---|---|---|
| 8,692,204 | B2 | 4/2014 | Kojima et al. |
| 8,698,093 | B1 | 4/2014 | Gubbens et al. |
| 8,716,662 | B1 | 5/2014 | MacDonald et al. |
| 9,222,895 | B2 | 12/2015 | Duffy et al. |
| 2008/0075352 | A1 | 3/2008 | Shibuya et al. |
| 2012/0323506 | A1 | 12/2012 | King |
| 2012/0323509 | A1* | 12/2012 | Chen .................. G06F 1/28 702/60 |
| 2015/0098655 | A1* | 4/2015 | Chang ............... G06K 9/00543 382/192 |
| 2015/0221076 | A1* | 8/2015 | Gao .................... G06T 7/001 382/149 |
| 2015/0262038 | A1* | 9/2015 | Konuru ............. G06T 7/0004 382/149 |
| 2017/0148226 | A1 | 5/2017 | Zhang et al. |
| 2017/0193680 | A1 | 7/2017 | Zhang et al. |
| 2017/0194126 | A1 | 7/2017 | Bhaskar et al. |
| 2017/0200260 | A1 | 7/2017 | Bhaskar et al. |
| 2017/0200265 | A1 | 7/2017 | Bhaskar et al. |

OTHER PUBLICATIONS

U.S. Appl. No. 15/603,249, filed May 23, 2017 by Zhang et al. (submitted as U.S. Patent Application Publication No. 2017/0345140 published Nov. 30, 2017).

\* cited by examiner

OPTIMIZING TRAINING SETS USED FOR SETTING UP INSPECTION-RELATED ALGORITHMS

BACKGROUND OF THE INVENTION

1. Field of the Invention

This invention generally relates to methods and systems for optimizing the training sets used for setting up inspection-related algorithms.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

When defects are detected on specimens such as wafers, often some type of algorithm is applied to the detected defects to separate them into different kinds of defects (or to separate defects from non-defects). One way to do that is to apply a defect classifier to the detected defects that separates the detected defects into different types or classes of defects. Defect classifiers usually use as input one or more attributes of the defects and/or the defect images (e.g., relatively small images acquired in the vicinity of the defects commonly called "patch" images or "patches") to determine the type or class of the defects. The defect classifiers then assign some type of identifier or ID to each defect that signifies its determined type or class. Another way to separate the detected defects is to separate actual defects from nuisance or noise. "Nuisance" defects are generally defined as defects that a user does not care about and/or defects that are detected as such but are not actually defects. Such algorithms are commonly referred to as defect filters and/or nuisance filters.

The most widely used classifiers/nuisance filters on optical inspection tools are based on manually-constructed decision trees. Tuning methods for these decision trees leverage experience and domain knowledge incorporated into best known methods (BKMs) for the tree construction. This typically results in the decision tree being initially constructed using the BKM "templates," defect clustering, and substantially crude defect labeling (using patches). After the structure of the tree has been obtained, the tree is then sampled diversely using diversity sampling with a smart sample distribution across the leaf nodes on the tree. The sampled defects are then scanning electron microscope (SEM) reviewed, classified, and used for final tuning of the decision cut lines (the boundaries separating different types of defects). Other classifiers based on machine learning algorithms (e.g., nearest neighbors type classifiers) find decision boundaries automatically given a training set, but no method currently exists for obtaining the training set that would maximize their performance.

There are, however, several disadvantages to the currently used methods for setting up and tuning defect classifiers. For example, the existing methods are labor intensive, require extensive expertise, and produce inconsistent results that are dependent on the human expert. Building classifiers by a human expert is prone to error and is costly and time consuming. Each defect has a relatively large number of features which make it virtually impossible to visualize the features properly for classification. Therefore, due to the lack of knowledge about the underlying multi-dimensional distributions, a human expert could make significant error in building the classification boundaries. Even without significant errors, the chance of creating sub-optimal classifiers manually is substantially high.

Accordingly, it would be advantageous to develop systems and/or methods for optimizing the training sets used for setting up inspection-related algorithms that do not have one or more of the disadvantages described above.

SUMMARY OF THE INVENTION

The following description of various embodiments is not to be construed in any way as limiting the subject matter of the appended claims.

One embodiment relates to a system configured to train an inspection-related algorithm. The system includes an inspection subsystem that includes at least an energy source and a detector. The energy source is configured to generate energy that is directed to a specimen. The detector is configured to detect energy from the specimen and to generate output responsive to the detected energy. The system also includes one or more computer subsystems. The one or more computer subsystems are configured for performing an initial training of an inspection-related algorithm with a labeled set of defects thereby generating an initial version of the inspection-related algorithm. The computer subsystem(s) are also configured for applying the initial version of the inspection-related algorithm to an unlabeled set of defects and altering the labeled set of the defects based on results of the applying. In addition, the computer subsystem(s) are configured for re-training the inspection-related algorithm with the altered labeled set of the defects thereby generating a more recent version of the inspection-related algorithm. The computer subsystem(s) are further configured for applying the more recent version of the inspection-related algorithm to another unlabeled set of the defects. In addition, the computer subsystem(s) are configured for determining one or more differences between results of applying the more recent version of the inspection-related algorithm and the results of applying the initial version or a less recent version of the inspection-related algorithm. The computer subsystem(s) are also configured for repeating altering the labeled set of the defects, re-training the inspection-related algorithm, applying the more recent version of the inspection-related algorithm, and determining the one or more differences until the one or more differences meet one or more criteria. When the one or more differences meet the one or more criteria, the computer subsystem(s) are configured for outputting a most recent version of the inspection-related algorithm as a trained inspection-related algorithm for use in inspection of other specimens. The system may be further configured as described herein.

Another embodiment relates to a computer-implemented method for training an inspection-related algorithm. The method includes steps for each of the functions of the one or more computer subsystems described above. The steps of the method are performed by one or more computer systems. The method may be performed as described further herein. In addition, the method may include any other step(s) of any other method(s) described herein. Furthermore, the method may be performed by any of the systems described herein.

An additional embodiment relates to a non-transitory computer-readable medium storing program instructions executed on a computer system for performing a computer-implemented method for training an inspection-related algorithm. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to train an inspection-related algorithm. In general, the embodiments described herein provide methods and systems for obtaining a minimal size training set for classifying defects captured by optical and other tools or for other inspection-related functions. In addition, the embodiments described herein advantageously can be used to find the minimal set of the most instructive defects for building classifiers and other inspection-related algorithms described herein for the purpose of defect classification and other inspection-related functions described herein.

The process of tuning specimen inspections (e.g., optical wafer inspections) for optimal performance has traditionally been almost entirely manual. Tuning processes generally rely on best known methods (BKMs) and on experience and skills of human experts that perform the tuning. Such approaches are therefore not desirable for setting up production monitoring systems not only because they are extremely costly (in effort and labor), but also because the outcome of tuning is subjective and lacks consistency. However, in spite of these obvious shortcomings of the current inspection tuning methodologies, attempts to automate this process have not found widespread acceptance in the production environment. The primary reason is that such automation relies on algorithms, which in turn derive their performance from the data on which they are trained (referred to as a training set). Therefore, unless the training data is acquired in a systematic way, the performance of these algorithms is uncertain. In other words, without a reliable method for finding a training set that optimizes the performance of the algorithms, such automated solutions suffer from all of the problems of the manual approaches. In particular, such solutions are not consistent, and their performance is not guaranteed to match that of the manual methods no matter how good the underlying algorithms are. In addition, it is frequently substantially difficult, if not impossible, to diagnose performance problems and to fix those problems when found. So it is of no surprise that machine learning approaches (as these approaches are known today) have not been successful so far.

The embodiments described herein provide a comprehensive tuning methodology for any machine learning algorithm that can be used for inspection-related functions like classification and filtering. (Even though the embodiments can be applied to detection algorithm tuning as well, the embodiments described herein are particularly useful for nuisance filters and classifiers.) The embodiments are based on the realization that for inspection (e.g., optical inspection) the approach for acquisition of the training set can be advantageously fully integrated with the algorithm tuning itself. The two are interlinked, and they should not be separated from each other to provide consistent behavior. The fundamental reason for this interdependence is as follows.

Inspection such as optical inspection is tuned using hot scans (highly defective scans with substantially high nuisance rates). Tuning itself requires labeled defects (i.e., classified defects, typically classified by a human expert). This classification is performed on scanning electron microscope (SEM) images that are acquired with a SEM review tool. If all defects detected in the hot scan could be reviewed and classified, there would be no need for the embodiments described herein. However, it is impossible in practice to do this, because this review/classification process is substantially expensive both in labor and tool time. So it is an absolute necessity to identify a suitable subset of defects that can produce optimal performance of the classifier or other inspection-related algorithm, and it is highly desirable to find a minimum set that achieves this.

The embodiments described herein provide methods and systems that optimize the selection of the training set of defects by means of learning iterations where the inspection-related algorithm (e.g., classifier model) learns the data and asks for what it needs to improve its performance. The embodiments described herein also advantageously provide methods and systems for determining the point at which the learning has reached its end.

In one embodiment, the specimen includes a wafer. In another embodiment, the specimen includes a reticle. The wafer and the reticle may include any wafer and reticle known in the art.

Figure 1:
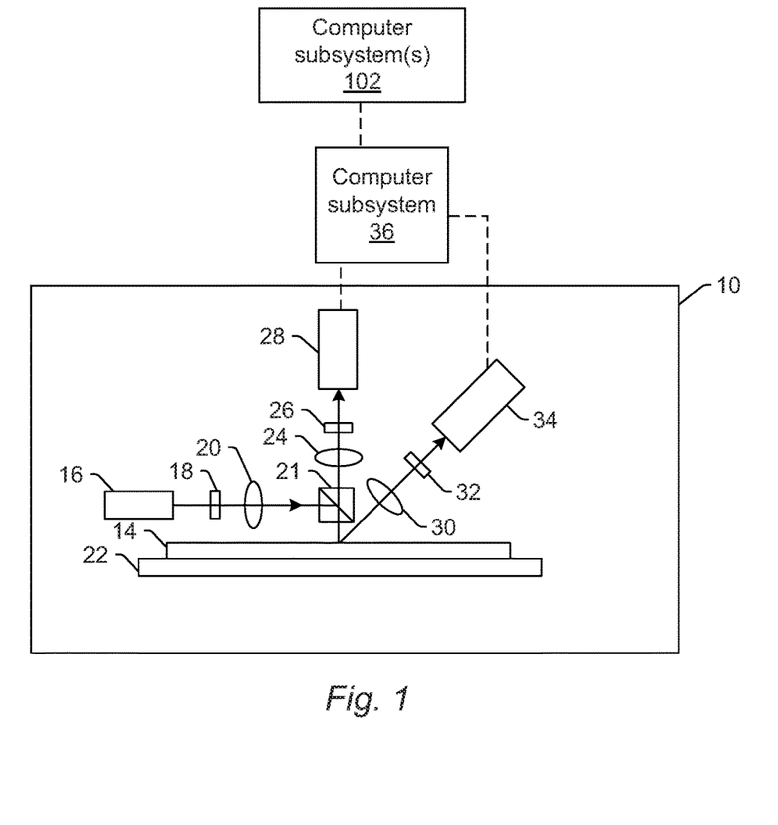
FIGS. 1 and 2 are schematic diagrams illustrating side views of embodiments of a system configured as described herein.

One embodiment of such a system is shown in FIG. 1. The system includes an inspection subsystem that includes at least an energy source and a detector. The energy source is configured to generate energy that is directed to a specimen. The detector is configured to detect energy from the specimen and to generate output responsive to the detected energy.

In one embodiment, the energy directed to the specimen includes light, and the energy detected from the specimen includes light. For example, in the embodiment of the system shown in FIG. 1, inspection subsystem 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to beam splitter 21, which directs the light to specimen 14 at a normal angle of incidence. The angle of incidence may include any suitable angle of incidence, which may vary depending on, for instance, characteristics of the specimen and the defects to be detected on the specimen.

The illumination subsystem may be configured to direct the light to the specimen at different angles of incidence at different times. For example, the inspection subsystem may be configured to alter one or more characteristics of one or more elements of the illumination subsystem such that the light can be directed to the specimen at an angle of incidence that is different than that shown in FIG. 1. In one such example, the inspection subsystem may be configured to move light source 16, optical element 18, and lens 20 such that the light is directed to the specimen at a different angle of incidence.

In some instances, the inspection subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection.

The inspection subsystem may also include a scanning subsystem configured to cause the light to be scanned over the specimen. For example, the inspection subsystem may include stage 22 on which specimen 14 is disposed during inspection. The scanning subsystem may include any suitable mechanical and/or robotic assembly (that includes stage 22) that can be configured to move the specimen such that the light can be scanned over the specimen. In addition, or alternatively, the inspection subsystem may be configured such that one or more optical elements of the inspection subsystem perform some scanning of the light over the specimen. The light may be scanned over the specimen in any suitable fashion.

The inspection subsystem further includes one or more detection channels. At least one of the one or more detection channels includes a detector configured to detect light from the specimen due to illumination of the specimen by the inspection subsystem and to generate output responsive to the detected light. For example, the inspection subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the specimen. However, two or more of the detection channels may be configured to detect the same type of light from the specimen (e.g., specularly reflected light). Although FIG. 1 shows an embodiment of the inspection subsystem that includes two detection channels, the inspection subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate image signals or image data. Therefore, the system may be configured to generate the output described herein in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the system as is normally performed when designing a commercial inspection system. In addition, the systems described herein may be implemented using an existing inspection system (e.g., by adding functionality described herein to an existing inspection system) such as the 28xx and 29xx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

Computer subsystem 36 of the system may be coupled to the detectors of the inspection subsystem in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number of functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Although the inspection subsystem is described above as being an optical or light-based inspection subsystem, the inspection subsystem may be an electron beam-based inspection subsystem. For example, in one embodiment, the energy directed to the specimen includes electrons, and the energy detected from the specimen includes electrons. In this manner, the energy source may be an electron beam source. In one such embodiment shown in FIG. 2, the inspection subsystem includes electron column 122, which is coupled to computer subsystem 124.

Figure 2:
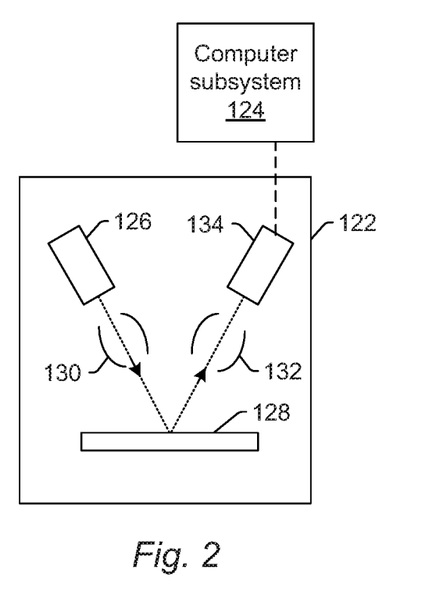

As also shown in FIG. 2, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 2 as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based subsystem may be configured to use multiple modes to generate images of the specimen (e.g., with different illumination angles, collection angles, etc.). The multiple modes of the electron beam-based subsystem may be different in any image generation parameters of the subsystem.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to perform any of the functions described herein using the output of the detector and/or the electron beam images. Computer subsystem 124 may be configured to perform any additional step(s) described herein. A system that includes the inspection subsystem shown in FIG. 2 may be further configured as described herein.

It is noted that FIG. 2 is provided herein to generally illustrate a configuration of an electron beam-based inspection subsystem that may be included in the embodiments described herein. As with the optical inspection subsystem described above, the electron beam-based inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system). For some such systems, the methods described herein may be provided as optional functionality of the system (e.g., in addition to other functionality of the system). Alternatively, the system described herein may be designed "from scratch" to provide a completely new system.

Although the inspection subsystem is described above as being a light- or electron beam-based inspection subsystem, the inspection subsystem may be an ion beam-based inspection subsystem. Such an inspection subsystem may be configured as shown in FIG. 2 except that the electron beam source may be replaced with any suitable ion beam source known in the art. In addition, the inspection subsystem may be any other suitable ion beam-based subsystem such as those included in commercially available focused ion beam (FIB) systems, helium ion microscopy (HIM) systems, and secondary ion mass spectroscopy (SIMS) systems.

The one or more computer subsystems described further herein may be coupled to the inspection subsystem that performs inspection of the specimen. For example, in one embodiment, the one or more computer subsystems are configured for detecting defects on the specimen based on the output generated by the detector. Alternatively, other one or more computer subsystems may be coupled to the inspection subsystem that performs inspection of the specimen. Such computer subsystem(s) may be configured as described further herein. In any case, one or more computer subsystems coupled to the inspection subsystem are configured for detecting defects on the specimen based on the output generated by one or more detectors of the inspection subsystem. The defects may be detected on the specimen in any suitable manner (e.g., by applying a threshold to the output and identifying output having one or more values above the threshold as a defect and not identifying output having one or more values below the threshold as a defect). The defects detected on the specimen may include any defects known in the art.

The computer subsystem(s) included in the systems described herein, however, do not necessarily detect defects on specimens. For example, the computer subsystem(s) may be configured to acquire results of an inspection of the specimen, which includes information for defects detected on the specimen. The results of the inspection of the specimen may be acquired by the computer subsystem(s) described herein directly from the system that performs the inspection (e.g., from a computer subsystem of the inspection system) or from a storage medium in which the inspection results have been stored such as a fab database.

As noted above, the inspection subsystem is configured for scanning energy (e.g., light or electrons) over a physical version of the specimen thereby generating actual images for the physical version of the specimen. In this manner, the inspection subsystem may be configured as an "actual" tool, rather than a "virtual" tool. For example, a storage medium (not shown) and computer subsystem(s) 102 shown in FIG. 1 may be configured as a "virtual" tool. In particular, the storage medium and the computer subsystem(s) are not part of inspection subsystem 10 and do not have any capability for handling the physical version of the specimen. In other words, in tools configured as virtual tools, the output of its one or more "detectors" may be output that was previously generated by one or more detectors of an actual tool and that is stored in the virtual tool, and during the "scanning," the virtual tool may replay the stored output as though the specimen is being scanned. In this manner, scanning the specimen with a virtual tool may appear to be the same as though a physical specimen is being scanned with an actual tool, while, in reality, the "scanning" involves simply replaying output for the specimen in the same manner as the specimen may be scanned. Systems and methods configured as "virtual" inspection tools are described in commonly assigned U.S. Pat. No. 8,126,255 issued on Feb. 28, 2012 to Bhaskar et al. and U.S. Pat. No. 9,222,895 issued on Dec. 29, 2015 to Duffy et al., both of which are incorporated by reference as if fully set forth herein. The embodiments described herein may be further configured as described in these patents. For example, the one or more computer subsystems described herein may be further configured as described in these patents. In addition, configuring the one or more virtual systems as a central compute and storage (CCS) system may be performed as described in the above-referenced patent to Duffy. The persistent storage mechanisms described herein can have distributed computing and storage such as the CCS architecture, but the embodiments described herein are not limited to that architecture.

As further noted above, the inspection subsystem may be configured to generate output for the specimen with multiple modes. In general, a "mode" can be defined by the values of parameters of the inspection subsystem used for generating output for a specimen. Therefore, modes that are different may be different in the values for at least one of the imaging parameters of the inspection subsystem. For example, in one embodiment of an optical based inspection subsystem, at least one of the multiple modes uses at least one wavelength of light for illumination that is different from at least one wavelength of the light for illumination used for at least one other of the multiple modes. The modes may be different in the illumination wavelength as described further herein (e.g., by using different light sources, different spectral filters, etc.) for different modes. In another embodiment, at least one of the multiple modes uses an illumination channel of the inspection subsystem that is different from an illumination channel of the inspection subsystem used for at least one other of the multiple modes. For example, as noted above, the inspection subsystem may include more than one illumination channel. As such, different illumination channels may be used for different modes.

As described further herein, the optical and electron beam subsystems described herein may be configured as inspection subsystems. However, the optical and electron beam subsystems described herein may be configured as other types of tools such as defect review subsystems. In particular, the embodiments of the inspection subsystem described herein and shown in FIGS. 1 and 2 may be modified in one or more parameters to provide different imaging capability depending on the application for which they will be used. In one such example, the inspection subsystem shown in FIG. 2 may be configured to have a higher resolution if it is to be used for defect review rather than for inspection. In other words, the embodiments of the inspection subsystem shown in FIGS. 1 and 2 describe some general and various configurations for an optical or electron beam subsystem that can be tailored in a number of manners that will be obvious to one skilled in the art to produce different subsystems having different imaging capabilities that are more or less suitable for different applications.

The one or more computer subsystems may be configured for acquiring the output for the specimen generated by an inspection subsystem described herein. Acquiring the output may be performed using one of the inspection subsystems described herein (e.g., by directing light or an electron beam to the specimen and detecting light or an electron beam, respectively, from the specimen). In this manner, acquiring the output may be performed using the physical specimen itself and some sort of imaging hardware. However, acquiring the output does not necessarily include imaging the specimen using imaging hardware. For example, another system and/or method may generate the output and may store the generated output in one or more storage media such as a virtual inspection system as described herein or another storage media described herein. Therefore, acquiring the output may include acquiring the output from the storage media in which they have been stored.

In one embodiment, the inspection-related algorithm is a defect classifier. For example, the algorithm may separate defects detected on a specimen into different types or classes of defects. The defect classifier may have any suitable configuration such as a decision tree or a nearest neighbor type configuration. In another embodiment, the inspection-related algorithm is a defect filter. The defect filter may be configured as a nuisance filter in that it may be configured to separate actual defects from nuisances (which may be defined as set forth further herein) and other noise and then eliminating (and thereby filtering) the nuisances and noise from the inspection results. The defect filter may also have any suitable configuration such as a decision tree or a nearest neighbor type configuration. In an additional embodiment, the inspection-related algorithm is a defect detection algorithm. The defect detection algorithm may be configured to perform defect detection as described further herein and/or in any other suitable manner known in the art. In a further embodiment, the inspection-related algorithm is a machine learning algorithm. The inspection-related algorithms described herein may be configured as machine learning algorithms. For example, defect classifiers, defect filters, and defect detection algorithms may have machine learning algorithm configurations. In addition, the machine learning algorithms may be configured as described in U.S. Patent Application Publication Nos. 2017/0148226 published May 25, 2017 by Zhang et al., 2017/0193680 published Jul. 6, 2017 by Zhang et al., 2017/0194126 published Jul. 6, 2017 by Bhaskar et al., 2017/0200260 published Jul. 13, 2017 by Bhaskar et al., and 2017/0200265 published Jul. 13, 2017 by Bhaskar et al., and U.S. patent application Ser. No. 15/603, 249 filed May 23, 2017 by Zhang et al., which are incorporated by reference as if fully set forth herein. The inspection-related algorithms described herein may have any configuration described in these publications.

Figure 3:
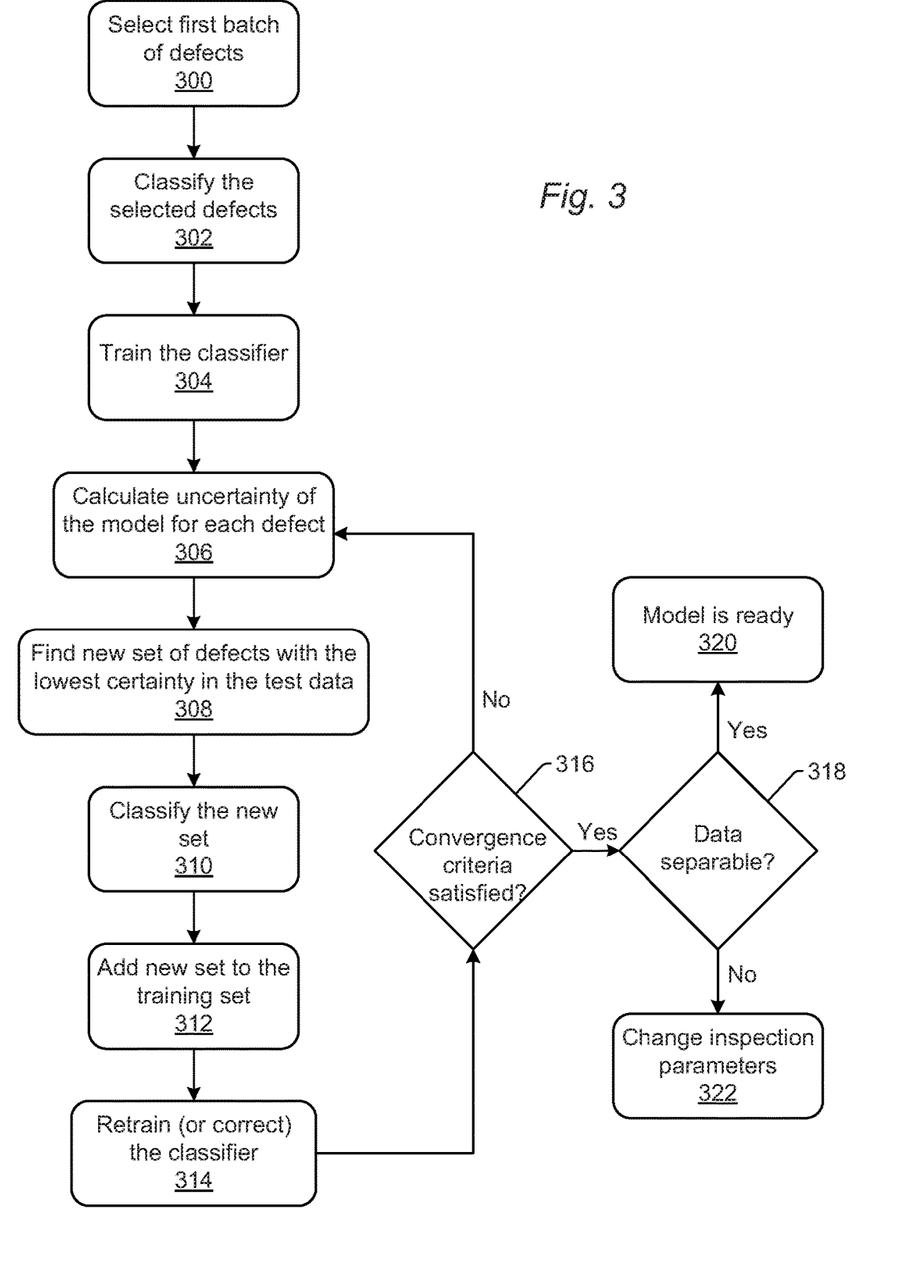
FIG. 3 is a flow chart illustrating one embodiment of steps that may be performed by the embodiments described herein.

The one or more computer subsystems are configured for performing an initial training of an inspection-related algorithm with a labeled set of defects thereby generating an initial version of the inspection-related algorithm. In some embodiments, the computer subsystem(s) may be configured to generate the labeled set of defects used for performing the initial training. For example, as shown in FIG. 3, the computer subsystem(s) may select first batch of defects as shown in step 300. The first batch of defects may be selected as described further herein. In addition, the computer subsystem(s) may classify the selected defects as shown in step 302. (Although FIG. 3 describes steps with respect to a defect classifier, the steps shown in FIG. 3 and described herein may be performed for a different inspection-related algorithm described herein.) The computer subsystem(s) may classify the selected defects and/or acquire classifications for the selected defects as described further herein. The computer subsystem(s) may then train the classifier as shown in step 304. The training performed in step 304 may therefore be the initial training described herein. The initial training may be performed in any suitable manner known in the art. For example, information for the defects such as attributes and/or images (or other detector output) may be input to the defect classifier, which may then classify the labeled defects. One or more parameters (e.g., cutlines, defect attributes, etc.) of the defect classifier may then be modified until the classifications produced for the defects by the defect classifier match the labels assigned to the defects. Although the defects may be labeled as described herein, defect attributes and defect patches (e.g., optical attributes and/or optical patches) may be used as input data for the inspection-related algorithm.

The computer subsystem(s) are also configured for applying the initial version of the inspection-related algorithm to an unlabeled set of defects. For example, once the inspection-related algorithm is initially trained on the labeled defects, the initial version of the inspection-related algorithm can be applied to the rest of the defects (and potential defects) that were detected by inspection of a specimen (which in a hot inspection of a wafer may include tens of thousands of defects) and that were not labeled.

In this manner, as described above, although the defects may be labeled as described herein, the attribute(s) and/or patch image(s) or other detector output are input to the inspection-related algorithm for the initial training. After the initial training on the labeled set (e.g., using the defects attribute(s) and/or patches or other detector output), the initial version of the inspection-related algorithm can be applied to the unlabeled set of defects. Applying the initial version of the inspection-related algorithm may be performed by inputting all (or some) of the information available for the unlabeled set of defects into the inspection-related algorithm. The unlabeled set of defects may be configured as described further herein.

The computer subsystem(s) are further configured for altering the labeled set of the defects based on results of the applying. For example, when the initial version of the inspection-related algorithm is applied to the unlabeled defects, the inspection-related algorithm may output not only the result for each of the unlabeled defects (e.g., a defect classification), but also a confidence of its decision (e.g., about the classification). This confidence may then be used in the defect selection process for the next iteration.

Defects that are selected in the defect selection process may be labeled as described further herein and then added to the labeled set of defects thereby altering the labeled set of defects. Altering the labeled set of the defects may be performed as described further herein.

In one embodiment, the labeled set of defects and the unlabeled set of defects are included in the same inspection results. For example, as described further herein, the labeled set of defects and the unlabeled set of defects may be produced by scanning one or more specimens. Such scanning may be performed as hot scans to thereby capture as many defects or defect types as possible. When the scanning includes hot scans, due to the volume of defects that are detected by such scanning, only one hot scan of only one specimen may produce enough defects for all steps that are described herein. Some of the defects detected by such scanning may be labeled as described herein to thereby produce the labeled set of defects (i.e., the training set of defects). The unlabeled set of defects may be the remaining defects detected by such scanning which are the unlabeled set of defects. Therefore, all of the defects detected by one or more hot scans may form the entirety of the defects used by the embodiments described herein, some of which are labeled and used for one or more steps described herein and others of which are not labeled and are used for one or more other steps described herein.

In another embodiment, altering the labeled set of defects includes labeling one or more of the defects in the unlabeled set and adding the labeled one or more of the defects to the labeled set. For example, one or more of the selected defects in the unlabeled set may be selected as described herein and then those one or more defects may be labeled in any suitable manner. In one such example, the one or more selected defects may be imaged by an image acquisition subsystem having a resolution higher than that of the inspection subsystem to thereby generate higher resolution images of the one or more selected defects. Those higher resolution defect images may then be provided to a user who assigns labels to the defects. However, as described further herein, the selected defects may be labeled by an automatic defect classifier (ADC). Therefore, the higher resolution defect images can also be provided to the user or to the ADC, one that operates on the higher resolution images. The labels that are assigned by the user may include any of the labels described herein such as defect, nuisance, noise, defect classification code, etc. The labels that are assigned by the user may vary depending on the configuration of the inspection-related algorithm. In some instances, the computer subsystem(s) may provide the user with a number of possible labels (e.g., defect, not defect, defect class code x, defect class code y, etc.). In addition, the computer subsystem(s) may enable a user to enter a new label such as a new defect class code, which may then be used to modify the configuration of the inspection-related algorithm (e.g., as when an inspection-related algorithm creates a new node, bin, definition, etc. for a new defect label). The labeled one or more of the defects may be added to the labeled set of defects in any suitable manner (e.g., by appending information for the newly labeled defect(s) to a file or other data structure in which information for the previously labeled defects is stored).

As described further herein, in one embodiment, the one or more computer subsystems are configured for detecting defects on the specimen based on the output generated by the detector, and the defects detected on the specimen include the labeled set of defects and the unlabeled set of defects. For example, the defects that are used by the computer subsystem(s) described herein may all be detected on a specimen or specimens by performing hot scan(s) on the specimen(s). In particular, for inspection such as optical inspections, nuisance filters and other inspection-related algorithms are typically trained on results of hot scans (i.e., specimen inspections that produce results containing tens of thousands of defects). A "hot scan" can be generally defined as an inspection performed on a specimen in which the threshold used for detecting potential defects and defects is set intentionally at or substantially near the noise floor of the output generated by the scanning. "Hot scans" are typically performed to detect as many potential defects and defects as possible to ensure that the most defects or all of the interesting defects are captured for purposes of inspection recipe setup and the like. Therefore, nuisance filters and other inspection-related algorithms may be trained using hot scan results.

To train an inspection-related algorithm such as a nuisance filter or defect classifier, a relatively small subset of defects detected on a specimen may be labeled. By labeling, we mean "classifying" those defects. "Classifying" the defects may vary depending on the inspection-related algorithm that is being trained or generated by the computer subsystem(s). For example, if the inspection-related algorithm is a defect detection algorithm, then the classifying may involve labeling detected defects as actual defects and not-actual defects (e.g., noise). In another example, if the inspection-related algorithm is a nuisance filter, then the classifying may involve labeling detected defects as actual defects and nuisance defects (which can be generally defined as noise and/or actual defects that the user does not actually care about). In a further example, if the inspection-related algorithm is a defect classifier, then the classifying may involve labeling the detected defects with defect IDs, e.g., class codes, that indicate different types of defects such as bridges, particles, scratches, missing features, roughness, etc. This defect classification or labeling may generally include first acquiring substantially high resolution images of the defects. The high resolution images may be generated using a SEM or high resolution optical imaging.

In one embodiment, the labeled set of defects used for the initial training includes a predetermined minimum number of defects selected from all defects detected on the specimen. For example, as described further herein, one of the advantages of the embodiments is that the labeled defects in the training set can be minimized without compromising the quality of the trained inspection-related algorithm. Therefore, the predetermined minimum number of labeled defects used for the initial training may be the smallest number of defects that is needed to produce a roughly trained initial version of the inspection-related algorithm. The minimum number of labeled defects can be predetermined heuristically or based on past experience and knowledge (e.g., about how many labeled defects are needed to train an inspection-related algorithm). In addition, the predetermined minimum number of labeled defects may vary depending on the inspection-related algorithm. For example, for a defect classifier, the predetermined minimum number of labeled defects may be a few (e.g., 2 or 3) defects of each defect type expected on the specimen and/or for which the classifier is configured. For a different inspection-related algorithm such as a defect detection algorithm or a nuisance filter, the predetermined minimum number of labeled defects may be several or tens of defects as well as non-defects (e.g., 10 to 50 of each). The predetermined minimum number of defects may be selected randomly from all of the defects available for use in the embodiments described herein and/or detected on the specimen (e.g., the unlabeled defects in the hot scan results). Those randomly selected defects may then be labeled as described herein. The labeled defects may then be analyzed to determine if the predetermined minimum number of labeled defects is sufficient for the initial training. If not enough of a particular type of defect have been selected and labeled, then the steps described above can be repeated until the sample of labeled defects includes the desired labeled defects in the desired numbers.

The embodiments described herein provide an iterative way for finding defects close to boundaries of underlying distributions. In addition, the embodiments described herein combine training set selection and defect labeling with the tuning process by having the inspection-related algorithm drive the selection process, which is believed to be a new idea particularly for optical inspections. For example, in a further embodiment, altering the labeled set of the defects includes determining certainty of the results produced for the defects in the unlabeled set by applying the initial version of the inspection-related algorithm, selecting the defects in the unlabeled set having the certainty that is the lowest, obtaining labels for the selected defects, and adding the selected defects and their labels to the labeled set of defects. For example, as shown in FIG. 3, the computer subsystem(s) may be configured for calculating uncertainty of the model, i.e., the inspection-related algorithm, for each defect as shown in step 306. In addition, the computer subsystem(s) may be configured for finding a new set of defects with the lowest certainty in the test data as shown in step 308. The computer subsystem(s) may be further configured for classifying the new set as shown in step 310. The computer subsystem(s) may also be configured for adding the new set to the training set as shown in step 312. In this manner, in these steps, after the inspection-related algorithm is initially trained with a substantially small set of labeled defects, the inspection-related algorithm (e.g., classifier) certainty about each defect can be measured. The certainty can be determined in any suitable manner. For example, the inspection-related algorithm may be configured to generate a confidence associated with each result that it generates (e.g., a confidence associated with each defect classification). That confidence may be used to determine the certainty. The inspection-related algorithm may also be configured to automatically produce a certainty for each result generated by the inspection-related algorithm. Then, the set of defects that the inspection-related algorithm is most uncertain about are selected and get labeled. The labeling (classification) of defects for the training set can be done manually using optical images (e.g., patches) or SEM images. The labeling can also be performed automatically using a pre-trained SEM automatic defect classifier (ADC). With reliable SEM ADC, this method would completely automate the training process and further speed up the recipe tuning process over the main construction ideas described herein. This new batch of labeled defects is added to the previously labeled defects and used to retrain (or correct) the inspection-related algorithm. Each of these steps may be performed as described further herein.

In one such embodiment, selecting the defects in the unlabeled set having the certainty that is the lowest includes selecting a predetermined minimum number of the defects in the unlabeled set having the certainty that is the lowest. For example, the defects in the unlabeled set may be selected from the defect that has the lowest certainty to the defect that has the next lowest certainty and so on until the predetermined minimum number has been met. The predetermined minimum number of the defects in the unlabeled set that are selected may be predetermined as described herein (e.g., heuristically or based on previous experiments and history to determine the minimum number of defects needed to achieve adequate training of the inspection-related algorithm).

In another such embodiment, selecting the defects in the unlabeled set having the certainty that is the lowest is performed independent of diversity in one or more characteristics of the defects in the unlabeled set. For example, the embodiments described herein may select the defects based on uncertainty of the labels assigned by the inspection-related algorithm without regard to diversity in a first characteristic of the defects, diversity in a second characteristic of the defects, or diversity in any other characteristic of the defects. In this manner, selecting defects based on the uncertainty of results produced for the defects by the inspection-related algorithm is different than diversity sampling. In addition, selecting the defects in the unlabeled set having the certainty that is the lowest may be performed without regard to any other attributes or information about the defects. However, when the inspection-related algorithm is configured to assign different labels to different previously unlabeled defects, the defects having the certainty that is the lowest may include defects assigned a first label and having the lowest certainties, defects assigned a second label and having the lowest certainties. In other words, selecting the defects in the unlabeled set having the lowest certainties without regard to diversity in one or more characteristics of the defects may be performed based on (or dependent on) labels assigned by the inspection-related algorithm. However, that selection is still not performed based on diversity of any one or more characteristics of the defects themselves. For example, the defects assigned to different labels and having the lowest certainties do not necessarily have values for any one characteristic of the defects that are relatively diverse. In fact, it may be similarity rather than diversity in any one characteristic of the defects that render them difficult to label by an initial, preliminary, or intermediate version of the inspection-related algorithm.

In some embodiments, altering the labeled set of the defects includes determining certainty of the results produced for the defects in the unlabeled set by applying the initial version of the inspection-related algorithm, selecting a group of the defects in the unlabeled set having the certainty that is the lowest, selecting a subset of the defects in the group having the greatest diversity in a characteristic of the defects in the subset, obtaining labels for the subset of the defects, and adding the selected subset of the defects and their labels to the labeled set of defects. For example, the embodiments described herein can combine uncertainty and diversity to make the sampling more efficient. The first priority is to sample the defects that the inspection-related algorithm is least confident about, because it is known that these are the defects that lie near the classification boundary and providing ground truth for these defects improves the quality of the inspection-related algorithm the most. However, when there are many "low confidence" defects, it may be advantageous to try to make sure that the computer subsystem(s) do not select essentially the same looking defects that would all have the same confidence but instead diversify the selected defects between many different low confidence defects. This way, the computer subsystem(s) may select the most diverse set around the classification boundary as opposed to just selecting many defects that are only in one part of the boundary. (The classification boundary is, in principle, complicated, unknown, and possibly hyper-plane in a multi-dimensional space, and to get an adequately trained inspection-related algorithm with the minimum number of labeled defects, the computer subsystem(s) preferably select the defects carefully around the entire boundary. In other words, the computer subsystem(s) preferably do not select defects that are relatively far from the classification boundary, i.e., have relatively high confidence, or are in the same part of the boundary, i.e., are not particularly diverse.)

The computer subsystem(s) are also configured for re-training the inspection-related algorithm with the altered labeled set of the defects thereby generating a more recent version of the inspection-related algorithm. For example, as shown in FIG. 3, the computer subsystem(s) may be configured for retraining (or correcting) the classifier as shown in step 314. The retraining may be performed as described further herein with respect to the initial training. In the retraining step, however, the retraining may start with the most previous version of the inspection-related algorithm (e.g., the parameters of the inspection-related algorithm produced by the initial training) or the first version of the inspection-related algorithm (e.g., the version of the inspection-related algorithm having pre-initial training parameters). In general though, when re-training the classifier after a new batch of defects were labeled and added to the training set, the re-training may start from the previous version of the classifier, but mostly the re-training starts from scratch. (A new classifier is simply trained on each new training set although either possibility can be done.) In this manner, the retraining may involve essentially training the inspection-related algorithm from scratch using a pre-initial-training version of the inspection-related algorithm or retraining the immediately prior version of the inspection-related algorithm by tuning and possibly fine tuning one or more parameters of the immediately prior version.

In addition, the computer subsystem(s) are configured for applying the more recent version of the inspection-related algorithm to another unlabeled set of the defects. The unlabeled set of defects to which the more recent version of the inspection-related algorithm is applied may include any and/or all of the remaining unlabeled defects available for use in the embodiments described herein and/or detected on the specimen or specimens. In this manner, the unlabeled set to which the more recent version is applied is different than the unlabeled set to which the initial version (or a previous version) is applied because one or more defects in the unlabeled set were selected, labeled, and added to the labeled set of defects. Therefore, the unlabeled set of defects to which the more recent version is applied may include fewer defects than the unlabeled set of defects to which the initial (or a previous) version is applied. However, in some instances, the unlabeled set of defects remaining after some have been selected, labeled, and added to the labeled set may be augmented with additional unlabeled defects if the number of the remaining unlabeled defects is not large enough. Augmenting the unlabeled set may be performed in any suitable manner such as by performing another hot scan on another specimen and/or acquiring additional inspection results from a storage medium, virtual system, etc. Generally, the scans described herein will provide sufficient unlabeled defects for the functions/steps described herein. Therefore, the more commonly performed augmentation will be augmentation of the labeled set if there are not enough such defects to thereby increase their number. The more recent version of the inspection-related algorithm may be applied to the other unlabeled set of the defects as described herein. For example, information for all or at least some of the defects in the other unlabeled set may be input to the more recent version of the inspection-related algorithm, which then produces results for each or at least some of the unlabeled defects in the set.

The computer subsystem(s) are also configured for determining one or more differences between results of applying the more recent version of the inspection-related algorithm and the results of applying the initial version or a less recent version of the inspection-related algorithm. The initial version of the inspection-related algorithm will be used for determining the differences when the more recent version is only the second version of the inspection-related algorithm that is generated (the version generated immediately after the initial version). In all other instances, the less recent version of the inspection-related algorithm used for determining the differences in this step may be the inspection-related algorithm generated immediately prior to the more recent version. In this manner, the differences may be determined between the most recently generated version of the inspection-related algorithm and the version generated immediately prior to that version. In other words, in this step, the differences may be determined between version n of the inspection-related algorithm and version n-1 of the inspection-related algorithm.

These differences are then used to determine if the process is converged as described further herein. For example, as described further herein, the process performed by the computer subsystem(s) may be determined to be converged when the changes in the classifications (or other results) between iterations becomes relatively small. The changes may not strictly be zero because of statistical fluctuations in the training process. In other words, when the training is repeated multiple times on the same training set, the exact same classification (or other result) may not be produced for the same defect. These small fluctuations can be estimated and when the changes between iterations become as small as this estimate, the process performed by the computer subsystem(s) can be stopped—it has converged. Also, when this criterion is reached, the inspection-related algorithm has achieved its maximum performance.

The computer subsystem(s) are further configured for repeating altering the labeled set of the defects, re-training the inspection-related algorithm, applying the more recent version of the inspection-related algorithm, and determining the one or more differences until the one or more differences meet one or more criteria. The one or more criteria therefore define the stopping criterion that terminates the iterations of labeling the defects and other steps described herein. For example, as described above, when the one or more differences are equal to or smaller than the estimate of the relatively small fluctuations that will occur from training to training regardless of the performance of the inspection-related algorithm, the one or more differences can be determined to meet the one or more criteria. In addition, different results produced by the inspection-related algorithm may have different criteria. For example, the one or more criteria for the differences in the results produced for one defect classification may be different than the one or more criteria for the differences in the results produced for another defect classification. In such instances, the steps described above may be repeated until all of the one or more criteria have been met. In other instances, all of the different results produced by the inspection-related algorithm may have the same criteria. For example, the one or more criteria for the differences in the results produced for different defect classifications may be the same. However, in such instances, the steps described above may also be repeated until all of the one or more criteria have been met. For example, the results produced for one defect classification may meet the one or more criteria sooner than the results produced for another defect classification even if the same one or more criteria need to be met for both defect classifications.

In one such example, as shown in FIG. 3, the computer subsystem(s) may be configured for determining if the convergence criteria is satisfied as shown in step 316. If the convergence criteria is not satisfied, then as shown in FIG. 3, the computer subsystem(s) may go back to step 306 and calculate uncertainty of the model (inspection-related algorithm) for each defect. The computer subsystem(s) may also repeat steps 308, 310, 312, and 314 shown in FIG. 3, until the convergence criteria has been determined to be satisfied. The reliance of the embodiments described herein on data-driven convergence criteria is believed to be new. In other words, as described further herein, a batch of unlabeled defects that the inspection-related algorithm (e.g., classifier) is least confident about can be selected. The selected defects can then be labeled as described herein. The newly labeled defects can be added to the training set, and the altered training set can be used to train a new inspection-related algorithm. These steps can be repeated until convergence has been met.

In one embodiment, the one or more criteria define a boundary between a) the one or more differences indicating the more recent version of the inspection-related algorithm is negligibly different than the initial version or the less recent version of the inspection-related algorithm and b) the one or more differences indicating the more recent inspection-related algorithm is significantly different than the initial version or the less recent version of the inspection-related algorithm. The one or more differences are those determined as described above (e.g., the differences between the version n of the inspection-related algorithm and the version n-1 of the inspection-related algorithm). In this manner, the computer subsystem(s) may track the history of the inspection-related algorithm after each iteration and if the changes in the results produced by the inspection-related algorithm are sufficiently small it terminates the iterations.

"Negligibly different" as that term is used herein may vary from inspection-related algorithm to inspection-related algorithm. However, "negligibly different" as used herein can be defined as any differences that are small enough to indicate that the inspection-related algorithm has not changed significantly from one version of the inspection-related algorithm to the next. Therefore, the difference(s) that qualify as "negligibly different" define the stopping criteria for the embodiments described herein. As such, the "negligibly different" values for the one or more differences may be predetermined and defined by a user (based on what their acceptable stopping criteria is) and/or may be predetermined by the computer subsystem(s) or another method or system based on general or specific information about the repeatability of the particular inspection-related algorithm being trained and/or the type of inspection-related algorithm being trained. The one or more differences that are "significantly different" as that term is used herein may be any and all differences other than the "negligibly different" values of the differences. In this manner, the one or more differences may have two different ranges of values: 1) the "negligibly different" ones defined as described herein; and 2) the "significantly different" ones that are all those other than the "negligibly different" ones.

If the changes are zero (or small) from the previous iteration to the current iteration, the computer subsystem(s) determine that there are not any new defects worth labeling since the inspection-related algorithm is certain about them.

In one particular example, the computer subsystem(s) may use the history of the changes of the predicted class codes of the defects in the last test data set. However, a number of other convergence measures can be considered for use in the embodiments described herein. All of the convergence measures may monitor some aspect of the classifier performance and/or the content of the training set as a function of the training iterations. For example, the computer subsystem(s) can monitor the inspection-related algorithm performance itself by tracking the accuracy as a function of iterations. Another method relies on monitoring the improvement in receiver operating curves (ROC) as a function of iterations. An ROC is basically a measure of performance of a binary classifier across the entire range of operating points (e.g., different nuisance rates). In addition, under certain circumstances, or for certain specific purposes, the computer subsystem(s) can monitor how different defect types are making it into the training set with each iteration, e.g., the computer subsystem(s) can stop when the computer subsystem(s) are no longer getting defects of interest (DOIs) into the training set.

When the one or more differences meet the one or more criteria, the computer subsystem(s) are configured for outputting a most recent version of the inspection-related algorithm as a trained inspection-related algorithm for use in inspection of other specimens. Outputting the most recent version of the inspection-related algorithm may include outputting the most recent trained parameters of the inspection-related algorithm possibly with the general configuration of the inspection-related algorithm when necessary. Outputting the most recent version of the inspection-related algorithm may also include storing the most recent version in a storage medium such as one of the storage media described herein and/or in an inspection recipe so that the inspection-related algorithm is executed when the inspection recipe is executed. (A "recipe" as that term is used herein can be generally defined as a set of instructions that can be used by a system to perform a process.)

In one embodiment, the one or more computer subsystems are configured for determining a measure of separability of different results produced by the most recent version of the inspection-related algorithm, and the outputting is performed only after the determined measure of separability is above a predetermined threshold. For example, inspection-related algorithms, e.g., nuisance filters (classifiers), are applied to data with various degrees of separability between data that corresponds to different things, e.g., defects vs. nuisance, one type of defect vs. another type of defect, etc. When separation between data is substantially good, then the inspection-related algorithm will generally achieve relatively good performance with relatively high confidence. When the separation in the data is mediocre or bad, the inspection-related algorithm does not perform as well and typically has a substantial amount of relatively low confidence results remaining no matter what is done. Therefore, the convergence criteria is not based on any measure of confidence or performance. The computer subsystem(s) may therefore simply monitor when the inspection-related algorithm stops improving, and at this point, the best inspection-related algorithm has been produced for this data. As such, a measure of separability may be determined for the most recent version of the inspection-related algorithm to determine if the best inspection-related algorithm that has been produced with the available training data is actually performing well enough to be used for other specimens. If the measure of separability is determined to be not sufficient, then other options such as other data produced with other output generation parameters of the inspection subsystem may be explored as alternative input to the inspection-related algorithm as described further herein.

In one such example, as shown in FIG. 3, once the convergence criteria is determined to have been satisfied in step 316, the computer subsystem(s) may determine if the data is separable as shown in step 318. If the data is determined to be separable in step 318, then in step 320 the computer subsystem(s) may determine that the inspection-related algorithm is ready (i.e., ready for use in inspection of other specimens, ready for use in production monitoring, etc.). In this manner, the embodiments may use a measure for assurance of the correctness of the inspection-related algorithm. To ensure that the inspection-related algorithm can separate the data correctly, the separability of the data may be measured. This measure tells if the data is separable. For an inspection-related algorithm that is a defect classifier, the measure may tell if the data is separable and if the classifier can classify each defect class better than a random guess or not. A correct classifier may be declared built if the data in the training set is separable. The data in the training set may be considered separable if the classifier's accuracy for each class code is above a certain threshold (e.g., somewhere above 50% (since accuracy of 50% on a balanced training set means completely random classification, i.e., no separability)).

If the computer subsystem(s) determine in step 318 of FIG. 3 that the data is not separable, then as shown in FIG. 3, the computer subsystem(s) may change inspection parameters as shown in step 322. For example, if the data is not separable, then in the case of defect classifiers, the data is not classifiable. In this case, the computer subsystem(s) may determine that one or more parameters of the inspection subsystem should be changed. For example, the computer subsystem(s) may determine that the inspection mode should be changed. The computer subsystem(s) may then perform the tuning of one or more parameters of the inspection subsystem or simply provide an instruction to another subsystem (computer or otherwise) that performs the tuning. The tuning or altering of the one or more parameters of the inspection subsystem may be performed in any suitable manner. Output generated using the tuned or altered parameter(s) of the inspection subsystem may then be used to generate a labeled set of defects and an unlabeled set of defects, which can then be used to perform the step(s) described herein to generate a trained inspection-related algorithm. In this manner, an inspection-related algorithm that is trained for the new parameter(s) of the inspection subsystem may be generated.

The embodiments described herein provide a number of advantages for training an inspection-related algorithm. For example, combining inspection-related algorithm tuning and training set acquisition into a single methodology provides huge advantages over existing approaches because the inspection-related algorithm tuning and training set acquisition described herein maximizes the effectiveness of the labeled defects for the performance of the inspection-related algorithm. (The labeled defects are the most instructive defects for training purposes, and thus the performance of the inspection-related algorithm is always optimal for the given data.) In addition, labeling defects (e.g., manually classifying them) is substantially expensive in terms of tool time and labor. Identifying the convergence criteria for the training set acquisition and the inspection-related algorithm tuning process minimizes the size of the training set and thus provides an advantage. Furthermore, the recognition that the process of combining training set selection and defect labeling with the tuning process is absolutely essential for application of any machine learning algorithms for optical inspection nuisance filters and classifiers is new. (Combining the training set selection and defect labeling with the tuning process is needed because the training data has tens of thousands of defects, most of which are nuisance.) The embodiments described herein also guarantee consistency of inspection recipes, i.e., nuisance filter tuning no longer depends on experience and skills.

Each of the embodiments of the system described herein may be combined with any other embodiments of the system described herein.

Another embodiment relates to a computer-implemented method for training an inspection-related algorithm. The method includes steps for each of the functions of the computer subsystem(s) described above. In particular, the method includes performing an initial training of an inspection-related algorithm with a labeled set of defects thereby generating an initial version of the inspection-related algorithm. The method also includes applying the initial version of the inspection-related algorithm to an unlabeled set of defects and altering the labeled set of the defects based on results of the applying. In addition, the method includes re-training the inspection-related algorithm with the altered labeled set of the defects thereby generating a more recent version of the inspection-related algorithm. The method further includes applying the more recent version of the inspection-related algorithm to another unlabeled set of the defects. The method also includes determining one or more differences between results of applying the more recent version of the inspection-related algorithm and the results of applying the initial version or a less recent version of the inspection-related algorithm. In addition, the method includes repeating altering the labeled set of the defects, re-training the inspection-related algorithm, applying the more recent version of the inspection-related algorithm, and determining the one or more differences until the one or more differences meet one or more criteria. When the one or more differences meet the one or more criteria, the method includes outputting a most recent version of the inspection-related algorithm as a trained inspection-related algorithm for use in inspection of other specimens.

Each of the steps of the method may be performed as described further herein. The method may also include any other step(s) that can be performed by the inspection subsystem and/or computer subsystem(s) or system(s) described herein. The steps of the method are performed by one or more computer systems, which may be configured according to any of the embodiments described herein. In addition, the method described above may be performed by any of the system embodiments described herein.

Figure 4:
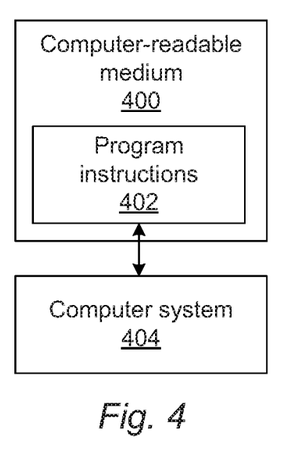
FIG. 4 is a block diagram illustrating one embodiment of a non-transitory computer-readable medium storing program instructions executed on a computer system for performing one or more of the computer-implemented methods described herein.

An additional embodiment relates to a non-transitory computer-readable medium storing program instructions executed on a computer system for performing a computer-implemented method for training an inspection-related algorithm. One such embodiment is shown in FIG. 4. In particular, as shown in FIG. 4, non-transitory computer-readable medium 400 includes program instructions 402 executable on computer system 404. The computer-implemented method may include any step(s) of any method(s) described herein.

Program instructions 402 implementing methods such as those described herein may be stored on computer-readable medium 400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 404 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, the trained inspection-related algorithm may be used to perform inspection(s) on other specimen(s), which may be performed as described herein. The results generated by the inspection(s) may be used to perform one or more functions for the other specimen(s) or the process that was used to form the other specimen(s). For example, the results generated by the inspection(s) performed using the inspection-related algorithm trained as described herein may be used to alter one or more parameters of one or more processes that were used to form the other specimen(s). In addition, or alternatively, the results generated by the inspection(s) performed using the inspection-related algorithm trained as described herein may be used to alter one or more parameters of one or more processes that will be performed on the other specimen(s) to either form additional features or materials on the other specimen(s) or to correct defects on the other specimen(s) thereby altering the other specimen(s) themselves.

Further modifications and alternative embodiments of various aspects of the invention will be apparent to those skilled in the art in view of this description. For example, methods and systems for training an inspection-related algorithm are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to train an inspection-related algorithm, comprising:
    an inspection subsystem comprising at least an energy source and a detector, wherein the energy source is configured to generate energy that is directed to a specimen, and wherein the detector is configured to detect energy from the specimen and to generate output responsive to the detected energy; and
    one or more computer subsystems configured for:
        performing an initial training of an inspection-related algorithm with a labeled set of defects thereby generating an initial version of the inspection-related algorithm;
        applying the initial version of the inspection-related algorithm to an unlabeled set of defects;
        altering the labeled set of the defects based on results of said applying;
        re-training the inspection-related algorithm with the altered labeled set of the defects thereby generating a more recent version of the inspection-related algorithm;
        applying the more recent version of the inspection-related algorithm to another unlabeled set of the defects;
        determining one or more differences between results of applying the more recent version of the inspection-related algorithm and the results of said applying the initial version or a less recent version of the inspection-related algorithm;
        repeating altering the labeled set of the defects, re-training the inspection-related algorithm, applying the more recent version of the inspection-related algorithm, and determining the one or more differences until the one or more differences meet one or more criteria; and
        when the one or more differences meet the one or more criteria, outputting a most recent version of the inspection-related algorithm as a trained inspection-related algorithm for use in inspection of other specimens.

2. The system of claim 1, wherein the inspection-related algorithm is a defect classifier.

3. The system of claim 1, wherein the inspection-related algorithm is a defect filter.

4. The system of claim 1, wherein the inspection-related algorithm is a defect detection algorithm.

5. The system of claim 1, wherein the inspection-related algorithm is a machine learning algorithm.

6. The system of claim 1, wherein the labeled set of defects and the unlabeled set of defects are included in the same inspection results.

7. The system of claim 1, wherein altering the labeled set of defects comprises labeling one or more of the defects in the unlabeled set and adding the labeled one or more of the defects to the labeled set.

8. The system of claim 1, wherein the one or more computer subsystems are further configured for detecting defects on the specimen based on the output generated by the detector, and wherein the defects detected on the specimen comprise the labeled set of defects and the unlabeled set of defects.

9. The system of claim 1, wherein the labeled set of defects comprises a predetermined minimum number of defects selected from all defects detected on the specimen.

10. The system of claim 1, wherein altering the labeled set of the defects comprises determining certainty of the results produced for the defects in the unlabeled set by said applying the initial version of the inspection-related algorithm, selecting the defects in the unlabeled set having the certainty that is the lowest, obtaining labels for the selected defects, and adding the selected defects and their labels to the labeled set of defects.

11. The system of claim 10, wherein selecting the defects in the unlabeled set having the certainty that is the lowest comprises selecting a predetermined minimum number of the defects in the unlabeled set having the certainty that is the lowest.

12. The system of claim 10, wherein selecting the defects in the unlabeled set having the certainty that is the lowest is performed independent of diversity in one or more characteristics of the defects in the unlabeled set.

13. The system of claim 1, wherein altering the labeled set of the defects comprises determining certainty of the results produced for the defects in the unlabeled set by said applying the initial version of the inspection-related algorithm, selecting a group of the defects in the unlabeled set having the certainty that is the lowest, selecting a subset of the defects in the group having the greatest diversity in a characteristic of the defects in the subset, obtaining labels for the subset of the defects, and adding the selected subset of the defects and their labels to the labeled set of defects.

14. The system of claim 1, wherein the one or more criteria define a boundary between a) the one or more differences indicating the more recent version of the inspection-related algorithm is negligibly different than the initial version or the less recent version of the inspection-related algorithm and b) the one or more differences indicating the more recent inspection-related algorithm is significantly different than the initial version or the less recent version of the inspection-related algorithm.

15. The system of claim 1, wherein the one or more computer subsystems are further configured for determining a measure of separability of different results produced by the most recent version of the inspection-related algorithm, and wherein said outputting is performed only after the determined measure of separability is above a predetermined threshold.

16. The system of claim 1, wherein the specimen comprises a wafer.

17. The system of claim 1, wherein the energy directed to the specimen comprises light, and wherein the energy detected from the specimen comprises light.

18. The system of claim 1, wherein the energy directed to the specimen comprises electrons, and wherein the energy detected from the specimen comprises electrons.

19. A non-transitory computer-readable medium, storing program instructions executed on a computer system for performing a computer-implemented method for training an inspection-related algorithm, wherein the computer-implemented method comprises:

performing an initial training of an inspection-related algorithm with a labeled set of defects thereby generating an initial version of the inspection-related algorithm;

applying the initial version of the inspection-related algorithm to an unlabeled set of defects;

altering the labeled set of the defects based on results of said applying;

re-training the inspection-related algorithm with the altered labeled set of the defects thereby generating a more recent version of the inspection-related algorithm;

applying the more recent version of the inspection-related algorithm to another unlabeled set of the defects;

determining one or more differences between results of applying the more recent version of the inspection-related algorithm and the results of said applying the initial version or a less recent version of the inspection-related algorithm;

repeating altering the labeled set of the defects, re-training the inspection-related algorithm, applying the more recent version of the inspection-related algorithm, and determining the one or more differences until the one or more differences meet one or more criteria; and     when the one or more differences meet the one or more criteria, outputting a most recent version of the inspection-related algorithm as a trained inspection-related algorithm for use in inspection of other specimens, wherein performing the initial training, applying the initial version, altering the labeled set, re-training the inspection-related algorithm, applying the more recent version, determining the one or more differences, said repeating, and said outputting are performed by the computer system.

20. A computer-implemented method for training an inspection-related algorithm, comprising:

performing an initial training of an inspection-related algorithm with a labeled set of defects thereby generating an initial version of the inspection-related algorithm;

applying the initial version of the inspection-related algorithm to an unlabeled set of defects;

altering the labeled set of the defects based on results of said applying;

re-training the inspection-related algorithm with the altered labeled set of the defects thereby generating a more recent version of the inspection-related algorithm;

applying the more recent version of the inspection-related algorithm to another unlabeled set of the defects;

determining one or more differences between results of applying the more recent version of the inspection-related algorithm and the results of said applying the initial version or a less recent version of the inspection-related algorithm;

repeating altering the labeled set of the defects, re-training the inspection-related algorithm, applying the more recent version of the inspection-related algorithm, and determining the one or more differences until the one or more differences meet one or more criteria; and     when the one or more differences meet the one or more criteria, outputting a most recent version of the inspection-related algorithm as a trained inspection-related algorithm for use in inspection of other specimens, wherein performing the initial training, applying the initial version, altering the labeled set, re-training the inspection-related algorithm, applying the more recent version, determining the one or more differences, said repeating, and said outputting are performed by one or more computer systems.

\* \* \* \* \*